United States Patent [19]

Chloupek et al.

[11] 3,953,537
[45] Apr. 27, 1976

[54] DISPROPORTIONATING C$_2$–C$_6$ PARAFFINS OVER ZEOLITES

[75] Inventors: Frank J. Chloupek, South Holland, Ill.; Robert A. Sanford, Prospect, Ky.; Laszlo Pollak, Chicago, Ill.; Ronald A. Kmecak, Ashland, Ky.

[73] Assignee: Atlantic Richfield Company, Philadelphia, Pa.

[22] Filed: Jan. 22, 1969

[21] Appl. No.: 793,173

[52] U.S. Cl. ........................... 260/676 R; 208/111; 260/676 MS; 260/683 R
[51] Int. Cl.$^2$ ..................... C07C 3/62; C07C 5/52; B01J 29/12
[58] Field of Search .......... 260/676 R, 672, 683.65, 260/683 D

[56] References Cited
UNITED STATES PATENTS

| | | | |
|---|---|---|---|
| 3,301,917 | 1/1967 | Wise | 260/683.65 |
| 3,392,212 | 7/1968 | d'Ouville | 260/676 X |
| 3,446,868 | 5/1969 | Box | 260/676 |
| 3,484,499 | 12/1969 | Lester et al. | 260/676 X |
| 3,668,268 | 6/1972 | Mulaskey | 260/676 R |
| 3,668,269 | 6/1972 | Chloupek | 260/676 R |
| 3,687,839 | 8/1972 | Jenkins | 208/111 |
| 3,812,199 | 5/1974 | Chen et al. | 260/676 R |
| B350,245 | 1/1975 | Lucki et al. | 260/676 R |

*Primary Examiner*—Delbert E. Gantz
*Assistant Examiner*—G. E. Schmitkons
*Attorney, Agent, or Firm*—Frank J. Uxa

[57] ABSTRACT

A process for disproportionating a paraffinic hydrocarbon containing 2 to 6 carbon atoms to produce paraffinic hydrocarbons containing one more and one less carbon fragment per molecule is disclosed. In the process the paraffinic hydrocarbon is contacted at about 400° to 1000°F. with an acidic, crystalline aluminosilicate catalyst having a pore size of about 8 to 15 A, silica to alumina mole ratio greater than 2 to 1 and at least about 0.4 equivalent per gram atom of aluminum of hydrogen or metal ion.

21 Claims, No Drawings

DISPROPORTIONATING $C_2$–$C_6$ PARAFFINS OVER ZEOLITES

The present invention relates to a process for converting paraffin feedstocks into desirable gasoline range hydrocarbons. More particularly, the present invention relates to a process whereby paraffin hydrocarbons of up to about 6 carbon atoms are disproportionated into higher and lower molcular weight paraffins, in the presence of a highly acidic crystalline aluminosilicate catalyst. Still more particularly, the present invention concerns a process whereby paraffin hydrocarbons of from 2 to about 6 carbon atoms are disproportionated into higher and lower molecular weight paraffins which differ from the feedstock by the addition or removal or one methane fragment.

In general, paraffins are noted for resistance to chemical conversions and as a class are considered relatively unreactive, with the lower molecular weight paraffins showing the greatest resistance to reactivity. Because of the lack of reactivity, paraffins, such as propane, butane, pentane, and the like, have found limited utility in chemical reactions or chemical processing although some of these paraffins can, for example, be cracked, isomerized, dehydrogenated, or alkylated, to produce more valuable products. For example, propane can be cracked to provide ethylene, with the loss of a methane fragment, or dehydrogenated to propylene, for utilization as an olefin in subsequent transformations.

It is an object of the present invention to provide a process whereby paraffin hydrocarbons are disproportionated to provide hydrocarbons of both higher and lower molecular weight, thereby providing additional uses for such paraffins. It is a further object to provide a process whereby a paraffin hydrocarbon feed is disproportionated on a strongly acidic crystalline aluminosilicate catalyst. It is a still further object to disproportionate a paraffin hydrocarbon feed so that two moles of paraffin feed provide one mole of paraffin product having one carbon atom more than the feed, and one mole of paraffin product having one carbon atom less than the paraffin feed. These and still other objects, as will become apparent, are realized by the process of the present invention.

In general, the process of the present invention comprises disproportionating a paraffin hydrocarbon feed by contacting with a highly acidic, crystalline aluminosilicate catalyst, under conditions of elevated temperature and pressure, to provide paraffins of higher and lower molecular weight. According to the present process, two moles of a paraffin hydrocarbon feedstock containing up to about 6 carbon atoms are reacted to provide one mole of paraffin product having one carbon atom more than the feed, and one mole of paraffin product having one carbon atom less than the parffin hydrocarbon feed. As an example, two moles of propane may be reacted to provide one mole of ethane and one mole of butane; butane can be reacted to provide propane and pentane, etc. By the present inventive process, a paraffin hydrocarbon of limited utility can be reacted to provide highly useful paraffin products, particularly paraffin boiling in the gasoline range and which are useful as fuels, solvents, and the like. The process of the present invention is highly effective in accomplishing the disproportionation of paraffins and, on a weight basis, yields of as much as 66% butane have been attained by the disproportionation of propane.

In the instant process, the paraffin hydrocarbon feed, i.e. having up to about 6, and preferably about 3 or 4, carbon atoms per mole is introduced into a reaction zone, which can be, for example, a fixed bed catalytic reactor, where it is contacted with a highly acidic, crystalline aluminosilicate catalyst at elevated temperature and pressure. The temperature will be within the range of about 400 to 1000°F., but ordinarily a more narrow range of temperature can be chosen to effect the greatest selectivity for a particular paraffin feed to the disproportionation reaction desired and to minimize undesirable side reactions, such as isomerization and cracking. The pressure can vary from atmospheric up to as much as about 3,000 p.s.i.g. or even higher but, ordinarily, it is preferable to utilize pressures from about 700 to 1600 p.s.i.g. The feed is contacted with the catalyst at weight hourly space velocities (WHSV) of from about 0.25 to 10, preferably about 0.5 to 4. The WHSV is ordinarily varied with the paraffin feed, the temperature, and the pressure, to give a high conversion level within an economically justifiable duration.

As the number of carbon atoms in the paraffin feed molecules increase, cracking is more likely to occur at a given temperature. In the instant process, cracking is an undesirable side reaction in direct conflict with the production of higher molecular weight paraffins which is a primary objective of the present invention. Cracking is also detrimental to catalyst activity and life due to the formation of coke. It is, therefore, desirable to operate the process of the present invention at temperatures which, while consonant with attaining high activity of the reaction and high conversion levels of the feed, are no higher than necessary, in order to avoid excessive cracking. It is possible to operate the process at a temperature whereat disproportionation occurs readily while little cracking takes place. Since cracking activity is favored at higher temperatures, the temperature is, accordingly desirably maintained at the lower end of the range providing for disproportionation, that is, at a temperature effective to avoid substantial or significant cracking of the feed. Since the reactivities of paraffin feeds vary with the number of carbon atoms per molecule, the specific temperature desired, will, of course, vary with the feed chosen. Generally, the fewer carbon atoms per molecule of the feed, the higher the temperature required to attain satisfactory disproportionation activity, and the higher the temperature which can be tolerated without significant cracking. Thus, for disproportionation of propane, relatively high temperatures of about 750° to 950°F. are particularly desirable, while for isopentane, lower temperatures on the order of about 450° to 800°F. are particularly desirable. In Table I, the general and preferred temperature ranges are indicated for disproportionation of a number of paraffin hydrocarbons. Within these ranges, no significant amounts of cracking occurs.

TABLE I

| Paraffin | CONVERSION TEMPERATURE, °F. | |
|---|---|---|
| | General | Preferred |
| propane | 750–950 | 800–850 |
| n-butane | 700–950 | 750–900 |
| isobutane | 600–900 | 700–850 |
| n-pentane | 500–800 | 550–750 |
| isopentane | 450–800 | 500–750 |

A second reaction of impact on the reaction of the present invention is isomerization since the catalysts used are relatively active for this reaction. It has been found, however, that disproportionation selectivity is generally higher for branched-chain paraffin hydrocarbons than for n-paraffins, suggesting that it is the branched isomers which disproportionate and that in this invention a n-paraffin feed is first isomerized to a branched chain isomer which, in turn, disproportionates.

The paraffin hydrocarbon feedstock in the process of the present invention can be substantially a single paraffin, such as propane, or can be a mixture of various paraffins containing up to about 6, and preferably 3 or 4, carbon atoms. The feed may be derived from petroleum fractions, such as are found in various petroleum refinery streams and can be separated in more or less pure form. Desirably, large amounts of olefins are excluded from the feed and, preferably, the feed will contain not more than about 5 percent by weight of olefins. Feeds essentially olefin free are particularly desirable. Among the paraffin hydrocarbons suited for the process of the present invention are methane, ethane, propane, n-butane, isobutane, n-pentane, isopentane, 2,2-dimethyl propane, n-hexane, 2-methyl pentane, 3-methyl pentane, 2,2-dimethyl butane, and 2,3-dimethyl butane. It is preferred to employ paraffin hydrocarbons of about 2 to 6, particularly 3 or 4 carbon atoms per molecule, including propane, n-butane, and isobutane.

The catalyst in the disproportionation reaction of the present invention can be either a synthetic or naturally-occurring crystalline aluminosilicate having not more than about 0.5 equivalents of alkali metal per gram atom of alumina in the crystalline aluminosilicate, and a pore size of about 8 to 15 A, preferably about 10 to 14 A. Usually, with a particular source of material, the pores are relatively uniform size. The aluminosilicate particles have an ultimate crystal size of about 0.5 to 15 microns, preferably about 0.5 to 1.5 microns. The silica-to-alumina mole ratio of the crystalline aluminosilicate is greater than about 2:1, and is usually not above about 11:1, preferably being about 4 to 6:1.

Crystalline aluminosilicates are available in a number of naturally occurring, alkali metal forms, such as, for example, faujasite and the like. For example, sodium crystalline aluminosilicates often have a sodium oxide-to-alumina ratio of about 0.7 to 1.1:1. Synthetic crystalline aluminosilicates are ordinarily prepared in alkali metal forms as well. The alkali metal serves as a catalyst poison and undue amounts should not be present in the catalyst used in the disproportionation reaction of the present invention. In the catalyst of the present invention, therefore, at least partial replacement of the alkali metal by hydrogen or by a polyvalent metal cation is necessary to provide a catalyst of desirable characteristics, that is, an acidic catalyst.

The catalyst utilized in the present invention can, for example, be prepared by base-exchanging the alkali metal crystalline aluminosilicate by treating with a solution characterized by a pH in excess of about 3, preferably by a pH in the range of about 4.5 to 10, and containing hydrogen, hydrogen precursor, or polyvalent metal cations which are capable of replacing the alkali metal. After treating to effect the exchange, the resultant base-exchanged material is washed free of water-soluble material, and the base-exchanged material is dried and subjected to a thermal activating treatment. The alkali metal content of the finished catalyst should be less than about 6, preferably less than about 3, weight percent. The base-exchange solution may be contacted with the alkali metal crystalline aluminosilicate in the form of a fine powder, a compressed pellet, extruded pellet, spheroidal bead, or other suitable particle form. The alkali metal aluminosilicate may be calcined prior to base-exchange in an atmosphere which does not adversely effect the aluminosilicate, such as air, nitrogen, hydrogen, flue gas, helium, or other inert gas, at a temperature in the range of about 500° to 1500°F. for a period of at least about one hour, and usually about one to forty eight hours.

The base-exchange required to introduce the necessary cations is carried out for an adequate period of time, a sufficient number of times, and at appropriate temperatures to effect replacement of at least about 50 weight percent, preferably about 60 to 90 weight percent, of the alkali metal originally contained in the aluminosilicate and to effectively reduce the alkali metal content of the resulting catalyst to below about 6 weight percent, preferably below about 3 weight percent. Stated another way, the finished catalyst contains less than about 0.5, preferably about 0.25, equivalents of alkali metal per gram atom of aluminum in the aluminosilicate.

It is contemplated that various ionizable compounds of hydrogen, hydrogen ion precursors, e.g. ammonium ions and the like, or of metals such as silver, copper, mercury and polyvalent metals can be used. The preferred polyvalent metals to be associated with the crystalline aluminosilicate employed as the catalyst of the present invention are the metals of Group IIA of the Periodic Table, i.e., beryllium, magnesium, calcium, strontium, barium, and radium. Also particularly suitable are the rare earth metals, including cerium, lanthanium, praseodymium, neodymium, illinium, samarium, europium, gadolinium, terbium, dryprosium, holmium, erbium, thulium, rytterbium, and lutecium. The metals can be used either singly or in combinations among themselves or with hydrogen ion precursors. Compounds are used where the polyvalent metal or hydrogen precursor is present as a cation. Inorganic salts will usually be employed, although organic salts, such as acetate and formate can also be used.

While water will ordinarily be the solvent in the base-exchange solutions used, it is contemplated that other solvents, although generally less preferred, can be used. Thus, in addition to aqueous solutions, alcoholic solutions and the like of suitable compounds can be employed in producing the catalyst utilized in the present invention. It will be understood that the compounds employed for the base-exchange solution undergo ionization in the particular solvent employed in the preparation.

The concentration of the compound employed in the base-exchange solution can vary, depending on the nature of the particular compound, on the alkali metal crystalline aluminosilicate undergoing treatment, and on the conditions under which the treatment is effected. Generally, the concentration of the compound supplying the polyvalent metal cation is within the range of about 0.2 to 30 weight percent although, as noted herein, other concentrations may be employed.

The temperature at which the base-exchange is effected may vary widely, generally ranging from room temperature to an elevated temperature below the boiling point of the treating solution. The volume of the base-exchange solution employed may vary widely, although generally an excess is employed and such excess is removed from contact with the crystalline aluminosilicate after a suitable period of contact. The time of contact between the base-exchange solution and the crystalline aluminosilicate in any instance, whether by a single or a plurality of successive contacts, is such as to effect displacement of the alkali metal ions to an extent such that the alkali metal content of the catalyst after base-exchange is satisfactorily reduced. It will be understood that such period of contact may vary, depending on the temperature of the solution, the nature of the crystalline aluminosilicate, and the particular compound employed for the base-exchange. Thus, the period of contact may extend from a brief period of on the order of a few hours for small particles to longer periods on the order of several days for large pellets.

After the base-exchange treatment, the catalyst is removed from the treating solution. Superfluous materials, such as anions introduced as a result of the treatment, are removed by water-washing the treated composite. The washed product is then dried, generally in air, to remove substantially all the water. While drying can be conducted at ambient temperatures, it is generally more satisfactory to facilitate the removal of moisture by maintaining the material at a temperature between about 150° and 600°F. for about 4 to 48 hours.

The dried material is then subjected to an activating treatment, essential to establish the catalytic activity of the composition. Such treatment entails heating the dried material in an atmosphere which does not adversely affect the catalyst, such as air, nitrogen, hydrogen, flue gases, helium, or other inert gas. The dried material can be heated, in air for example, to a temperature in the approximate range of about 500° to 1500°F. for a period of at least about one hour, and usually about one to forty eight hours.

The active aluminosilicate component prepared in the foregoing manner can be combined, dispersed or otherwise intimately admixed with a porous matrix in such proportions that the resulting product contains from about 5 to 95 weight percent, preferably about 15 to 80 weight percent, of the active aluminosilicate in the final composite. The incorporation of the crystalline aluminosilicate into the porous matrix can be accomplished before, after, or during the base-exchange treatment. Particularly preferred matrices are inorganic oxide gels such as alumina and silica-alumina because of their superior porosity, attrition resistance, and stability under reaction conditions.

The following examples serve to further illustrate the process of the present invention.

EXAMPLE I

A calcium-exchanged crystalline aluminosilicate containing catalyst was prepared from a synthetic faujasite 1/16 inch extrudate containing sodium aluminosilicate crystallites having pores of about 13 A and a silica-alumina mole ratio of about 4.5 and about 20 weight percent of alumina monohydrate. The faujasite was calcined at 1050°F. for 3 hours prior to calcium exchange treatments. The calcined material contained 6.87 weight percent sodium and 1.57 weight percent volatilizable material at 1000°C. The aluminosilicate was base-exchanged with two portions of an aqueous solution of calcium nitrate at 150°F., followed by a water wash to remove essentially all nitrate ions, drying, and calcining for three hours at 900°F. The calcined catalyst contained 5.53 weight percent calcium, 2.11 weight percent sodium and 3.51 weight percent volatile material at 1000°F.

One hundred grams of the calcium-exchanged crystalline aluminosilicate-alumina catalyst were charged to a univeral type reactor and heater under a nitrogen purge at 1000 psig. Propane was introduced by a LS-20 Lapp pump from a calibrated, pressurized blow case. The nitrogen purge was discontinued as the propane feed was introduced. The reactor effluent was condensed in a dry ice trap and analyzed by vapor phase chromatography. Untrapped gases were analyzed by mass spectrometry. The conditions employed and the results of the analysis appear in Table II as Run No. 1.

Additional Runs, Nos. 2–6, were made using the same catalyst and procedure as in Run No. 1, varying the feed, temperatures, weight, hourly space velocities, and other conditions as stated.

TABLE II

| Run No. | 1 | 2 | 3 | 4 | 5 | 6 |
|---|---|---|---|---|---|---|
| Feed | $C_3$ | $C_3$ | $n\text{-}C_4$ | $i\text{-}C_4$ | $n\text{-}C_5$ | $i\text{-}C_5$ |
| WHSV | 0.515 | 0.451 | 0.535 | 3.95 | 1.97 | 2.06 |
| Temp.,°F. | 850 | 750 | 745 | 845 | 600 | 601 |
| Pres.,psig | 1000 | 1000 | 1000 | 1000 | 1000 | 1000 |
| % Conv. on Feed | 20.09 | 5.6 | 37.8 | 37.9 | 13.4 | 29.3 |
| Wt. % Selectivity | | | | | | |
| $C_2^-$ | 25.6 | 14.7 | — | — | — | — |
| $C_3^=$ | 1.0 | 0.7 | — | — | — | — |
| $C_3^-$ | — | — | 24.2 | 24.7 | 1.5 | 1.5 |
| $C_4$ | 58.5 | 64.7 | 43.4 | 41.8 | 10.6 | 27.9 |
| $C_5$ | 7.9 | 14.4 | 24.0 | 27.0 | 81.6 | 31.7 |
| $C_6$ | 1.5 | 5.5 | 2.5 | 3.2 | 6.1 | 33.2 |
| $C_7$ | — | — | 0.1 | 0.9 | 0.2 | 3.1 |
| $C_8+$ | — | — | — | 0.2 | — | 0.6 |
| Coke | 5.5 | — | 5.8 | 2.2 | — | 1.9 |
| i/n Ratio | | | | | | |
| $C_4$ | 0.69 | 0.87 | — | — | 5.12 | 8.33 |
| $C_5$ | — | — | 1.71 | 2.98 | — | — |
| $C_6$ | — | — | 3.42 | 4.58 | 4.10 | 10.00 |
| $C_2^-/C_4+$ wt. ratio | 0.356 | 0.160 | — | — | — | — |
| $C_2^-/C_4+$ mole ratio | 1.21 | 0.616 | | | | |
| $C_3^-/C_5+$ wt. ratio | | | | | 0.797 | |
| $C_3^-/C_5+$ mole | | | | | | |

TABLE II-continued

| Run No. | 1 | 2 | 3 | 4 | 5 | 6 |
|---|---|---|---|---|---|---|
| ratio | | | | 1.528 | | |

EXAMPLE II

In Example II a series of runs were conducted using seven different base-exchanged crystalline aluminosilicates and one crystalline sodium aluminosilicate. In these runs, the feed was C.P. grade, 99.45 percent assay isobutane for catalyst A, technical grade isobutane for catalysts B through E and 98.5 percent isobutane for catalysts F through H. The conditions were maintained in each run at about 750°F., 1000 psig. and 2.0 WHSV on a 30 gram catalyst charge.

The catalyst compositions utilized were the following:

A. 5 weight percent hydrogen-exchanged crystalline aluminosilicate with 95 weight percent amorphous silicaalumina, extruded into 1/8 pellets.

B. 80 weight percent calcium-exchanged crystalline aluminosilicate with 20 weight percent alumina monohydrate, extruded to 1/16 inch pellets. This catalyst is the same as that used in Example I.

C. 80 weight percent mixed rare earth metal-exchanged crystalline aluminosilicate and 20 weight percent alumina monohydrate, as 1/16 inch extrudate, calcined at 1050°F.

D. 5 weight percent mixed rare earth metal-exchanged crystalline aluminosilicate and 95 weight percent amorphous silica alumina, as beads.

E. 15 weight percent hydrogen-exchanged crystalline aluminosilicate and 85 weight percent amorphous silica-alumina in the form of 1/16 inch extrudate.

F. 50 weight percent hydrogen-exchanged crystalline aluminosilicate with 50 weight percent alumina monohydrate, in 1/8 inch pellets.

G. Catalyst F, steamed for 24 hours at 1050°F.

H. 80 weight percent crystalline sodium aluminosilicate and 20 weight percent alumina monohydrate, as 1/6 inch extrudate.

The catalysts were utilized in the disproportionation of isobutane, utilizing the process of the present invention as indicated in Example I. The results of the runs made with each catalyst are reported in Table III. Designations are as defined above in Table II.

In Table III, the designations of results have the following meaning:

Conversion, $iC_4$ = wt. % disappearance of isobutane
Conversion, $C_4$—s = wt. % isobutane converted by disproportionation
Selectivites,
L/H Ratio = mole ratio of the lighter paraffin hydrocarbon to the heavier produced by disproportionation
Isom/Disp. Ratio = weight ratio of isomerization product to disproportionation product
Disp. No. = $\dfrac{(\text{mole \%}\ C_5) \times 2}{\text{Mole \%}\ C_4\ \text{conversion}}$
Isom. No. = $\dfrac{\text{\% isomers}}{\text{\% feed converted}}$
Crack. No. = 1 − [Disp. N.. + Isom. No.]

TABLE III

Catalyst Testing Data
Catalyst A

| Sample No. | 1 | 2 | 3 | 4 |
|---|---|---|---|---|
| Temp. °F. | 755 | 749 | 751 | 753 |
| WHSV | 2.02 | 2.02 | 2.02 | 1.98 |
| Conversions, $iC_4$ | 40.63 | 34.08 | 34.93 | 34.53 |
| Conversions, $C_4$—s | 21.37 | 16.22 | 16.71 | 16.57 |
| Selectivities, L/H | | | | |
| Ratio (Moles) | 0.937 | 0.934 | 0.922 | 0.916 |
| Isom/Disp. | | | | |
| Ratio (Wt.) | 0.901 | 1.101 | 1.090 | 1.083 |
| Catalyst Activities | | | | |
| Disp. No. | 0.492 | 0.471 | 0.476 | 0.477 |
| Isom. No. | 0.474 | 0.524 | 0.521 | 0.520 |
| Crack No. | 0 | 0 | 0 | 0 |

TABLE III

Catalyst Testing Data
Catalyst B

| Sample No. | 1 | 2 | 4 |
|---|---|---|---|
| Temp. °F. | 747 | 746 | 753 |
| WHSV | 1.90 | 1.91 | 1.91 |
| Conversions, $iC_4$ | 70.21 | 53.28 | 49.41 |
| Conversions, $C_4$—s | 43.89 | 28.32 | 30.55 |
| Selectivities, L/H | | | |
| Ratio (Moles) | 1.765 | 1.292 | 0.538 |
| Isom/Disp. | | | |
| Ratio (Wt.) | 0.599 | 0.881 | 0.617 |
| Catalyst Activities | | | |
| Disp. No. | 0.399 | 0.448 | 0.718 |
| Isom. No. | 0.375 | 0.468 | 0.381 |
| Crack No. | 0.226 | 0.084 | 0 |

TABLE III

Catalyst Testing Data
Catalyst C

| Sample No. | 1 | 2 | 3 | 4 |
|---|---|---|---|---|
| Temp. °F. | 740 | 750 | 756 | 756 |
| WHSV | 2.20 | 2.11 | 1.89 | 1.98 |
| Conversions, $iC_4$ | 48.34 | 47.63 | 48.92 | 45.61 |
| Conversions, $C_4$—s | 26.34 | 24.96 | 25.93 | 23.93 |
| Selectivities, L/H | | | | |
| Ratio (Moles) | 0.981 | 1.098 | 0.963 | 0.855 |
| Isom/Disp. | | | | |
| Ratio (Wt.) | 0.835 | 0.908 | 0.988 | 0.906 |
| Catalyst Activities | | | | |
| Disp. No. | 0.525 | 0.508 | 0.524 | 0.541 |
| Isom. No. | 0.455 | 0.475 | 0.469 | 0.4757 |
| Crack No. | 0 | 0.017 | 0 | 0 |

TABLE III

Catalyst Testing Data
Catalyst D

| Sample No. | 1 | 2 | 3 | 4 |
|---|---|---|---|---|
| Temp. °F. | 740 | 746 | 749 | 749 |
| WHSV | 2.20 | 2.13 | 1.94 | 1.98 |
| Conversions, $iC_4$ | 36.38 | 32.47 | 33.69 | 32.85 |
| Conversions, $C_4$—s | 19.61 | 16.35 | 17.16 | 16.82 |
| Selectivities, L/H | | | | |
| Ratio (Moles) | 0.896 | 1.049 | 0.095 | 0.981 |
| Isom/Disp. | | | | |
| Ratio (Wt.) | 0.855 | 0.985 | 0.963 | 0.953 |
| Catalyst Activities | | | | |
| Disp. No. | 0.528 | 0.482 | 0.480 | 0.504 |
| Isom. No. | 0.460 | 0.496 | 0.490 | 0.487 |
| Crack No. | 0 | 0.022 | 0.030 | 0 |

TABLE III

Catalyst Testing Data — E

| Sample No. | 1 | 2 | 3 | 4 |
|---|---|---|---|---|
| Temp. °F. | 742 | 746 | 750 | 747 |
| WHSV | 1.80 | 1.87 | 2.00 | 1.98 |
| Conversions, iC$_4$ | 62.83 | 56.68 | 57.27 | 49.71 |
| Conversions, C$_4$—s | 36.33 | 30.87 | 27.12 | 26.20 |
| Selectivities, L/H |  |  |  |  |
| Ratio (Moles) Isom/Disp. | 1.949 | 1.148 | 1.355 | 1.388 |
| Ratio (Wt.) | 0.729 | 0.836 | 0.890 | 0.897 |
| Catalyst Activities |  |  |  |  |
| Disp. No. | 0.373 | 0.482 | 0.438 | 0.415 |
| Isom. No. | 0.421 | 0.455 | 0.471 | 0.472 |
| Crack No. | 0.206 | 0.063 | 0.091 | 0.113 |

TABLE III

Catalyst Testing Data — F

| Sample No. | 1 | 2 | 3 | 4 |
|---|---|---|---|---|
| Temp. °F. | 740 | 750 | 750 | 755 |
| WHSV | 2.10 | 2.04 | 1.98 | 2.02 |
| Conversions, iC$_4$ | 66.63 | 54.90 | 52.38 | 47.82 |
| Conversions, C$_4$—s | 42.97 | 32.52 | 31.20 | 27.82 |
| Selectivities, L/H |  |  |  |  |
| Ratio (Moles) Isom/Disp. | 2.731 | 1.960 | 1.664 | 1.506 |
| Ratio (Moles) | 0.550 | 0.657 | 0.678 | 0.716 |
| Catalyst Activities |  |  |  |  |
| Disp. No. | 0.324 | 0.395 | 0.423 | 0.434 |
| Isom No. | 0.355 | 0.389 | 0.404 | 0.417 |
| Crack No. | 0.321 | 0.216 | 0.173 | 0.149 |

TABLE III

Catalyst Testing Data — G

| Sample No. | 1 | 2 |
|---|---|---|
| Temp. °F. | 753 | 756 |
| WHSV | 2.03 | 1.98 |
| Conversions, iC$_4$ | 22.89 | 25.52 |
| Conversions, C$_4$—s | 10.98 | 12.65 |
| Selectivities, L/H |  |  |
| Ratio (Moles) Isom/Disp. | 1.146 | 1.017 |
| Ratio (Wt.) | 1.084 | 1.018 |
| Catalyst Activities |  |  |
| Disp. No. | 0.424 | 0.456 |
| Isom. No. | 0.520 | 0.504 |
| Crack No. | 0.056 | 0.049 |

TABLE III

Catalyst Testing Data — H

| Sample No. | 1 | 2 | 3 |
|---|---|---|---|
| Temp. °F. | 740 | 748 | 749 |
| WHSV | 1.90 | 1.90 | 1.98 |
| Conversions, iC$_4$ | 2.04 | 0.54 | 0.72 |
| Conversions, C$_4$—s | 1.12 | 0.28 | 0.32 |

It is clear from the analyses reported in Table III that the polyvalent metal-exchanged crystalline aluminosilicates are active to disproportionate paraffin hydrocarbons. It is also clear that the alkali metal crystalline aluminosilicate has no appreciable activity for the disproportionation of paraffin hydrocarbons.

It is claimed:

1. A process for disproportionating a paraffinic hydrocarbon containing up to about 6 carbon atoms to produce compounds containing one more and one less carbon fragment per molecule than said paraffinic hydrocarbon which comprises contacting said paraffinic hydrocarbon at conditions sufficient for disproportionation of said hydrocarbon and insufficient to cause substantial cracking of the hydrocarbon said contacting occurring at a temperature in the range of about 400° to 1,000°F., with a crystalline aluminosilicate having a pore size of about 10 to 14 Angstrom units and a silica to alumina mole ratio greater than about 3 to 1 to about 11 to 1, said catalyst containing less than about 0.5 equivalent of alkali metal per gram atom of aluminum and at least about 0.4 equivalent per gram atom of aluminum in the aluminosilicate of hydrogen or metal ion, said metal ion being selected from the group consisting of silver, copper, mercury, polyvalent metals, and mixtures thereof, and recovering said paraffin hydrocarbons containing one more and one less carbon fragment.

2. The process of claim 1 wherein the contact of said paraffinic hydrocarbon with said catalyst is conducted at a pressure of up to about 3000 atmospheres and a weight hourly space velocity of about 0.25 to about 10.

3. The process of claim 1 wherein the paraffinic hydrocarbon has from 2 to 6 carbon atoms.

4. The process of claim 1 wherein metal ion is present in the aluminosilicate, the metal ion is a polyvalent metal ion and said contacting occurs at a pressure in the range from about 700 to 1600 psig.

5. The process of claim 4 wherein the polyvalent metal is a Group IIA metal.

6. The process of claim 5 wherein the polyvalent metal ion is calcium.

7. The process of claim 4 wherein the polyvalent metal ion is a rare earth metal.

8. The process of claim 1 wherein said catalyst contains less than about 0.25 equivalents of alkali metal per gram atom of aluminum.

9. The process of claim 2 wherein the paraffin hydrocarbon feed is n-butane and the conversion temperature is about 700° to 950°F.

10. The process of claim 2 wherein the paraffin hydrocarbon feed is isobutane and the conversion temperature is about 600° to 900°F.

11. The process of claim 10 wherein said temperature is about 700° to 850°F.

12. The process of claim 2 wherein the paraffin hydrocarbon feed is n-pentane and the conversion temperature is about 500° to 800°F.

13. The process of claim 12 wherein said temperature is about 550° to 750°F.

14. The process of claim 2 wherein the paraffin hydrocarbon feed is isopentane and the conversion temperature is about 450° to 800°F.

15. The process of claim 14 wherein said temperature is about 500° to 750°F.

16. The process of claim 1 wherein the paraffinic hydrocarbon feed is a mixture of paraffins.

17. The process of claim 16 wherein the mixture comprises a C$_3$ paraffin and a C$_4$ paraffin.

18. The process of claim 1 wherein the crystalline aluminosilicate is faujasite.

19. A process for disproportionating n-butane to produce compounds containing one more and one less carbon fragment per molecule than said n-butane which comprises contacting said n-butane at conditions sufficient for disproportionation of said n-butane and insufficient to cause substantial cracking of the n-butane said contacting occurring at a temperature in the range of about 700° to 900°F., a pressure of up to about 3,000 atmospheres and a weight hourly space velocity of about 0.25 to about 10 with a crystalline aluminosilicate having a pore size of about 8 to 15 Angstrom units and a silica to alumina mole ratio greater than about 2 to 1, said catalyst containing less than about 0.5 equivalent of alkali metal per gram atom of aluminum and at least about 0.4 equivalent per gram atom of aluminum in the aluminosilicate of hydrogen or metal ion, said metal ion being selected from the group consisting of silver, copper, mercury, polyvalent metals, and mixtures thereof, and recovering said paraffin hydrocarbons containing one more and one less carbon fragment.

20. A process for disproportionating a paraffinic hydrocarbon containing up to about 6 carbon atoms to produce compounds containing one more and one less carbon fragment per molecule than said paraffinic hydrocarbon which comprises contacting said paraffinic hydrocarbon at conditions sufficient for disproportionation of said hydrocarbon and insufficient to cause substantial cracking of the hydrocarbon said contacting occurring at a temperature in the range of about 400° to 1,000°F., with a crystalline aluminosilicate having a pore size of about 8 to 15 Angstrom units and a silica to alumina mole ratio greater than about 2 to 1, said catalyst containing less than about 0.5 equivalent of alkali metal per gram atom of aluminum and at least about 0.4 equivalent per gram atom of aluminum in the aluminosilicate of hydrogen, and recovering said paraffin hydrocarbons containing one more and one less carbon fragment.

21. The process of claim 20 wherein the contacting of said paraffinic hydrocarbon with said catalyst is conducted at a pressure of about 3,000 atmospheres and a weight hourly space velocity of about 0.25 to about 10.

* * * * *